United States Patent [19]

Crowley

[11] Patent Number: 4,567,199

[45] Date of Patent: Jan. 28, 1986

[54] HALOBENZYL ESTERS

[75] Inventor: Patrick J. Crowley, Bracknell, England

[73] Assignee: Imperial Chemical Industries PLC, London, England

[21] Appl. No.: 539,570

[22] Filed: Oct. 6, 1983

Related U.S. Application Data

[63] Continuation of Ser. No. 336,585, Jan. 4, 1982, abandoned.

[30] Foreign Application Priority Data

Jan. 21, 1981 [GB] United Kingdom ............... 8101825
Aug. 27, 1981 [GB] United Kingdom ............... 8126204

[51] Int. Cl.$^4$ .................... C07C 69/743; A01N 53/00
[52] U.S. Cl. .................................. 514/531; 560/124
[58] Field of Search .................. 560/124; 424/305; 514/531

[56] References Cited

U.S. PATENT DOCUMENTS

| | | | |
|---|---|---|---|
| 3,792,079 | 2/1974 | D'Orazio | 560/124 |
| 4,183,950 | 1/1980 | Naumann | 560/124 |
| 4,243,677 | 1/1981 | Engel | 560/124 |
| 4,252,820 | 2/1981 | Lantzsch | 560/124 |
| 4,259,349 | 3/1981 | Bull | 560/124 |
| 4,385,070 | 5/1983 | Bentley | 560/124 |
| 4,423,066 | 12/1983 | Fuchs | 560/118 |

FOREIGN PATENT DOCUMENTS 1078511  8/1967  United Kingdom ............... 560/124

OTHER PUBLICATIONS

Huff, UK Patent Application, 2,034,700A (6-11-1980).

Primary Examiner—Michael L. Shippen
Attorney, Agent, or Firm—Cushman, Darby & Cushman

[57] ABSTRACT

Compounds of formula I where Q is fluoro, chloro or bromo and R is monochloromonofluorobenzyl, and compositions containing them, useful as insecticides particularly for controlling soil pests. A typical example is that wherein Q is chloro and R is 2-chloro-6-fluorobenzyl.

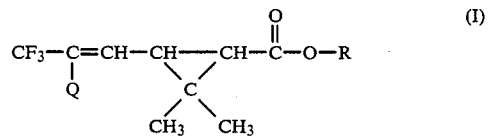

6 Claims, No Drawings

HALOBENZYL ESTERS

This is a continuation of application Ser. No. 336,585 filed Jan. 4, 1982 now abandoned.

This invention relates to novel cyclopropane esters useful as insecticides.

UK Patent Application No. 2034700A discloses difluorobenzyl esters of 3-(2-chloro-3,3,3-trifluoroprop-1-en-1-yl)-2,2-dimethylcyclopropane carboxylic acid and their use as insecticides. European Patent Application No. 003336A2 discloses the compound 2,6-dichlorobenzyl(±)-trans-3-(2-chloro-3,3,3-trifluoroprop-1-en-1-yl)-2,2-dimethylcyclopropane carboxylate.

We have now discovered that certain chlorofluorobenzyl esters of 3-(2-halo-3,3,3-trifluoroprop-1-en-1-yl)-2,2-dimethylcyclopropane acids have surprisingly better insecticidal properties in some tests when compared with the above known compounds.

The invention provides novel compounds of formula:

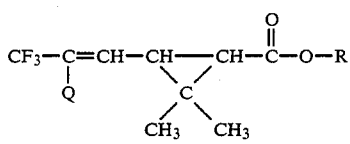
(I)

wherein Q represents fluoro, chloro or bromo and R represents a group of formula:

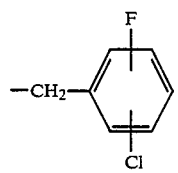

It will be appreciated by those skilled in the art that the compounds represented by formula I are capable of existing in various geometrical and stereoisomeric forms. Thus there may be cis and trans isomers arising from the substitution pattern of the cyclopropane ring, and E- and Z-isomers arising from the substituted vinyl group when $R^1$ is not identical with $R^2$. In addition two of the three carbon atoms of the cyclopropane are capable of existing in either R- or S-configurations since they are asymmetrically substituted.

Particular compounds include those set out in the following table wherein the meanings for Q and R in formula (I) are given together with an indication of the isomeric composition of each compound.

TABLE I

| COMPOUND NO | Q | R | ISOMERIC COMPOSITION |
| --- | --- | --- | --- |
| 1 | Cl | 2-chloro-4-fluorobenzyl | Z(±)-cis |
| 2 | Cl | 2-chloro-6-fluorobenzyl | Z(±)-cis |
| 3 | F | 2-chloro-4-fluorobenzyl | Z(±)-trans |
| 4 | Cl | 2-chloro-6-fluorobenzyl | Z(±)-trans |
| 5 | Cl | 2-chloro-4-fluorobenzyl | Z(±)-trans |
| 6 | F | 2-chloro-4-fluorobenzyl | Z(±)-cis |
| 7 | F | 2-chloro-6-fluorobenzyl | Z(±)-cis |
| 8 | F | 2-chloro-6-fluorobenzyl | Z(±)-trans |
| 9 | Cl | 2-chloro-5-fluorobenzyl | Z(±)-cis |
| 10 | F | 2-chloro-5-fluorobenzyl | Z(±)-trans |
| 11 | F | 2-chloro-5-fluorobenzyl | Z(±)-cis |

TABLE I-continued

| COMPOUND NO | Q | R | ISOMERIC COMPOSITION |
| --- | --- | --- | --- |
| 12 | Cl | 2-chloro-6-fluorobenzyl | Z(±)-cis/trans |

Within the group of compounds represented by Formula I the cis isomers usually have better insecticidal properties than the trans isomers or the mixture of cis and trans isomers; the (+)-cis isomers being particularly preferred.

A particularly useful single isomer of a compound according to the invention is the 2-chloro-6-fluorobenzyl ester of (+)-cis-3-(Z-2-chloro-3,3,3-trichloroprop-1-en-yl)-2,2-dimethylcyclopropane carboxylic acid, which is believed to have the (1R,3R) configuration in the cyclopropane ring.

The compounds of the invention according to Formula I are esters and may be prepared by conventional esterification processes, of which the following are examples.

(a) An acid of formula:

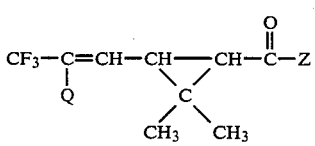
(I)

where Z represents the hydroxy group and Q has any of the meanings given hereinabove, may be reacted directly with an alcohol of formula:

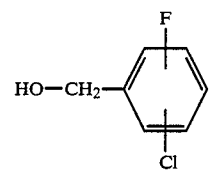
(III)

the reaction preferably taking place in the presence of an acid catalyst, for example, dry hydrogen chloride.

(b) An acid halide of formula II where Z represents a halogen atom, preferably a chlorine atom, and Q has any of the meanings given hereinabove, may be reacted with an alcohol of formula III, the reaction preferably taking place in the presence or a base, for example, pyridine, alkali metal hydroxide or carbonate, or alkali metal alkoxide.

(c) An acid of formula II where Z represents the hydroxy group and Q has any of the meanings given hereinabove, or preferably, an alkali metal salt thereof, may be reacted with halide of formula:

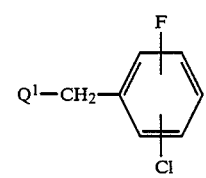
(IV)

where $Q^1$ represents a halogen atom, preferably the bromine or chlorine atom, or with the quaternary ammonium salts derived from such halides with tertiary amines, for example pyridine, or trialkyl amines such as triethylamine.

(d) A lower alkyl ester of formula II where Z represents a lower alkoxy group containing up to six carbon atoms, preferably the methoxy or ethoxy group, and Q has any of the meanings given hereinabove, is heated with an alcohol of formula III to effect a transesterification reaction. Preferably the process is performed in the presence of a suitable catalyst, for example, an alkali metal alkoxide, such as sodium methoxide, or an alkylated titanium derivative, such as tetramethyl titanate.

All of these conventional processes for the preparation of esters may be carried out using solvents and diluents for the various reactants where appropriate, and may be accelerated or lead to higher yields of product when performed at elevated temperatures or in the presence of appropriate catalysts, for example phase-transfer catalysts.

The preparation of individual isomers may be carried out in the same manner but commencing from the corresponding individual isomers of compounds of formula II. These may be obtained by conventional isomer separation techniques from mixtures of isomers. Thus cis and trans isomers may be separated by fractional crystallisation of the carboxylic acids or salts thereof, whilst the various optically active species may be obtained by fractional crystallisation of salts of the acids with optically active amines, followed by regeneration of the optically pure acid. The optically pure isomeric form of the acid (or its equivalent acid chloride or ester) may then be reacted with the appropriate alcohol to produce a compound of formula I in the form of an individually pure isomer thereof.

The preparation of the compounds of formula II wherein Z is hydroxy, alkoxy or halo, and $R^1$ and $R^2$ are as defined hereinabove, useful as intermediates in the preparation of the compounds of the invention, is fully described in British Patent Specification No. 2,000,764 and in U.S. Pat. No. 4,183,948.

The compounds of this invention may be formulated for use and used as insecticides in the ways indicated for the compounds of UK Patent Application No. 2034700A. The compounds are particularly useful for the control of insect pests which inhabit the soil including Agrotis spp, Agriotis spp and Diabrotica spp. For this purpose they are preferably formulated as granules in which the insecticidally active esters are supported (eg. by coating or impregnation) on mineral, e.g. pumice or gypsum, granules, or granules of vegetable matter e.g. those derived from corn cobs. They are applied to soil at rates of 0.05 to 25 kg/ha (based on active ingredient), and preferably at rates of 0.1 to 15 kg/ha. Because the invention compounds have high intrinsic activity against the pests and are also capable of exerting this activity over a prolonged period only one application is required in the course of a growing season to give effective control. The granules may contain from 0.5 to 2.5% by weight of the active ingredient, and the stability of the granules may be improved and the rate of release of the active ingredient may be regulated by the incorporation of a resin or coating with a polymeric substance e.g. a polyvinyl alcohol based material. The granules may be applied to the surface of the soil adjacent to the furrow in which the plants are growing, and may be lightly incorporated in the soil thereafter, or the granules may be placed in the furrows with the seed at the time of planting.

The following Examples illustrate the invention.

EXAMPLE 1

Preparation of 2-chloro-4-fluorobenzyl bromide

A solution of bromine (7.10 ml) in carbon tetrachloride (70 ml) was added slowly over a period of 3 hours to a solution of 2-chloro-4-fluorotoluene (20.0 g) in carbon tetrachloride (80 ml) maintained at the reflux temperature and irradiated by light from a tungsten lamp (200 watt). After the addition was completed the mixture was heated at the reflux temperature with irradiation until the colour had been discharged (ca.1 hour). The solvent was then removed by evaporation under reduced pressure and the residual oil distilled to yield 2-chloro-4-fluorobenzyl bromide (80% pure, 18.0 g) b.p. 110°–120° C./15 mm Hg.

N.m.r. ($CDCl_3$): 2.59–2.76 (m,1H); 2.80–3.20 (m,2H); 5.46 (s,2H)τ.

EXAMPLE 2

Preparation of 2-chloro-4-fluorobenzyl(±)-cis-3-(Z-2-chloro-3,3,3-trifluoroprop-1-en-1-yl)-2,2-dimethylcyclopropane carboxylate A mixture of (±)-cis-3-(Z-2-chloro-3,3,3-trifluoroprop-1-en-1-yl)-2,2-dimethylcyclopropane carboxylic acid (1.20 g), anhydrous potassium carbonate (2.0 g), 2-chloro-4-fluorobenzyl bromide (1.10 g), and dry acetone (30 ml) was stirred for a period of 2 hours at the ambient temperature (ca 25° C.) and kept at that temperature for a further 18 hours. After diluting the mixture with diethyl ether (300 ml) the resultant mixture was washed with dilute aqueous sodium carbonate solution and dried over anhydrous magnesium sulphate. The solvents were evaporated and the residual oil purified by preparative thick layer chromatography using silica gel plates and chloroform eluent, to give 2-chloro-4-fluorobenzyl(±)-cis-3-(Z-2-chloro-3,3,3-trifluoroprop-1-en-1-yl)-2,2-dimethylcyclopropane carboxylate (1.31 g) as a colourless oil.

N.m.r. ($CDCl_3$)τ: 2.56–2.70 (q,1H); 2.82–3.15 (m,3H); 4.81 (s,2H); 7.68–8.01 (m,2H); 8.66 (s,6H).

Infra red (liquid film): 1720 $cm^{-1}$.

EXAMPLE 3

Preparation of 2-chloro-6-fluorobenzyl(±)-cis-3-(Z-2-chloro-3,3,3-trifluoroprop-1-en-1-yl)-2,2-dimethylcyclopropane carboxylate A mixture of (±)-cis-1-chlorocarbonyl-3-(Z-2-chloro-3,3,3-trifluoroprop-1-en-1-yl)-2,2-dimethylcyclopropane (0.82 g), 2-chloro-6-fluorobenzyl alcohol (1.0 g), pyridine (0.275 g) and dry toluene (50 ml) was stirred at the ambient temperature (ca. 25° C.) for a period of 6 hours and then kept for a further period of 72 hours without stirring. The mixture was diluted with diethyl ether (350 ml) and the resultant mixture washed with water, with dilute aqueous sodium carbonate solution, and then dried over anhydrous magnesium sulphate. The solvents were evaporated and the residual oil purified by preparative thick layer chromatography using silica gel plates and diethyl ether as eluent. The oil which was obtained was then distilled to yield 2-chloro-6-fluorobenzyl(±)-cis-3-(Z-2-chloro-3,3,3-trifluoroprop-1-en-1-yl)-2,2-dimethylcyclopropane carboxylate (0.67 g) b.p. 150°/0.05 mm Hg.

N.m.r. (CDCl₃)τ: 2.60–3.06 (m,3H); 3.14 (d,1H); 4.76 (s,2H); 7.80–8.12 (m,2H); 8.75 (s,6H).
Infra red (liquid film): 1720 cm⁻¹.

EXAMPLE 4

The remaining compounds of the invention were prepared by methods analogous to those illustrated in Examples 2 and 3 from the appropriate cyclopropane carboxylic acids and benzyl halides or alcohols. All of the compounds showed n.m.r. and infra-red spectral data consistant with the assigned structures.

2-Chloro-4-fluorobenzyl(±)-3-(Z-2,3,3,3-tetrafluoroprop-1-en-1-yl)-2,2-dimethylcyclopropane carboxylate (Compound no.3, Table I). Oil.
N.m.r.(CDCl₃)δ: 1.3 (d,6H); 1.75 (d,1H); 2.3 (q,1H); 5.2 (s,2H); 5.3 (dd,1H); 7.2 (m,3H) ppm
Infra red (liquid film): 3060, 1720, 1600, 1590, 1130 cm⁻¹

2-Chloro-6-fluorobenzyl(±)-trans-3-(Z-2-chloro-3,3,3-trifluoroprop-1-en-1-yl)-2,2-dimethylcyclopropane carboxylate (Compound no.4, Table 1). Oil.
N.m.r. (CDCl₃)δ: 1.3 (d,6H); 1.8 (d,1H); 2.4 (m,1H); 5.3 (d,2H); 6.1 (d,1H); 7.1 (m,3H) ppm
Infra red (liquid film): 1720 cm⁻¹

2-Chloro-4-fluorobenzyl(±)-trans-3-(Z-2-chloro-3,3,3-trifluoroprop-1-en-1-yl)-2,2-dimethylcyclopropane carboxylate (Compound no.5, Table I). Oil.
N.m.r.(CDCl₃)δ: 1.30 (d,6H); 1.8 (d,1H); 2.5 (m,1H); 5.25 (s,2H); 6.2 (d,1H); 7.2 (m,3H) ppm
Infra red (liquid film): 1720 cm⁻¹

2-Chloro-4-fluorobenzyl(±)-cis-3-(Z-2,3,3,3-tetrafluoroprop-1-en-1-yl)-2,2-dimethylcyclopropane carboxylate Compound no.6, Table I). Oil.
N.m.r.(CDCl₃)δ: 1.25 (s,6H); 2.10 (m,2H); 5.20 (s,2H); 6.10 (dd,1H); 7.2 (m,3H) ppm
Infra red (liquid film): 3060, 1720, 1600, 1130 cm⁻¹

2-Chloro-6-fluorobenzyl(±)-cis-3-(Z-2,3,3,3-tetrafluoroprop-1-en-1-yl)-2,2-dimethylcyclopropane carboxylate (compound no.7, Table I). Oil.
N.m.r.(CDCl₃)δ: 1.25 (d,6H); 2.0 (m,2H); 5.3 (d,2H); 6.1 (dd,1H); 7.2 (m,3H) ppm
Infra red (liquid film): 3060, 1720, 1600, 1570, 1130 cm⁻¹

2-Chloro-6-fluorobenzyl(±)-trans-3-(Z-2,3,3,3-tetrafluoroprop-1-en-1-yl)-2,2-dimethylcyclopropane carboxylate (compound no.8, Table I). Oil.
N.m.r.(CDCl₃)δ: 1.2 (s,3H); 1.3 (s,3H); 1.7 (d,1H); 2.35 (q,1H); 5.34 (d,2H); 5.3 (dd,1H); 7.2 (m,3H).
Infra red (liquid film): 3060, 1720, 1600, 1573, 1130

2-Chloro-5-fluorobenzyl(±)-cis-3-(Z-2-chloro-3,3,3-tetrafluoroprop-1-en-1-yl)-2,2-dimethylcyclcopropane carboxylate (compound no.9, Table I). Oil.
N.m.r.(CDCl₃)δ: 1.32 (s,6H); 2.02–2.30 (m,2H); 5.12 (s,2H); 6.84–7.44 (m,4H)
Infra red (liquid film): 1722 cm⁻¹

2-Chloro-5-fluorobenzyl(±)-trans-3-(Z-2,3,3,3-trifluoroprop-1-en-1-yl)-2,2-dimethylcyclopropane carboxylate (compound no.10, Table I). Oil.
N.m.r.(CDCl₃)δ: 2.24 (s,3H); 2.35 (s,3H); 1.76 (d,1H); 2.36 (dd,1H); 5.12 (s,2H); 5.30 (dd,1H); 6.85–7.46 (m,3H)
Infra red (liquid film): 1725 cm⁻¹

2-Chloro-5-fluorobenzyl(±)-cis-3-(Z-2,3,3,3-tetrafluoroprop-1-en-1-yl)-2,2-dimethylcyclopropane carboxylate (compound no.11, Table I). Oil
N.m.r.(CDCl₃)δ: 1.30 (s,6H); 1.90–2.30 (m,2H); 5.24 (s,2H); 6.14 (dd,1H); 6.84–7.46 (m,3H)
Infra red (liquid film): 1725 cm⁻¹

2-chloro-6-fluorobenzyl(±)-cis/trans-3-(Z-2-chloro-3,3,3-trifluoroprop-1-en-1-yl)-2,2-dimethylcyclopropane carboxylate (compound no. 12, Table I; 50/50 cis/trans mixture). Oil.
N.m.r. (CDCl₃)δ: 1.19 (s,1;2H); 1,24 (s,1.5H); 1.32 (s,1.5H); 1.78 (d,0.5H); 1.9–2.28 (m,1H); 2.30–2.56 (m.0.5H); 5.30 (bs,2H); 6.19 (d,0.5H); 6.90–7.44 (m,3.5H).
Infra red (liquid film): 1727 cm⁻¹

EXAMPLE 5

This Example illustrates the insecticidal properties of the compounds of formula I against the larval stage of the rootworm *Diabrotica balteata*. The compound under test was dissolved in acetone and the solution diluted with acetone until the required concentration (500, 100, 12 or 10 ppm) was obtained. 1.0 ml of the solution thus obtained is applied to a filter paper (9 cm diameter) which is air dried to allow the solvent to evaporate and then placed in a petri dish. 1.0 ml of water is added and 10 early second instar larval *Diabrotica balteata* are placed on the filter paper together with a germinating maize seed. A lid is placed on the dish which is stored at 25° C. and 60% relative humidity for 72 hours after which time the mortality of the larvae is assessed.

The results of the tests are given in Table II for each of the compounds tested at the rate in parts per million given as a grading of mortality on a scale of 0–9 wherein
0 represents less than 10% mortality
1 represents from 10 to 19% mortality
2 represents from 20 to 29% mortality
3 represents from 30 to 39% mortality
4 represents from 40 to 49% mortality
5 represents from 50 to 59% mortality
6 represents from 60 to 69% mortality
7 represents from 70 to 79% mortality
8 represents from 80 to 89% mortality
9 represents from 90 to 100% mortality

TABLE II

| | MORTALITY GRADING | |
|---|---|---|
| COMPOUND NO | 100 ppm (*500 ppm) | 10 ppm (*12 ppm) |
| 1 | 9 | 9 |
| 2 | 9 | 9 |
| 3 | 9 | 9* |
| 4 | 9 | 9* |
| 5 | 9 | 9* |
| 6 | 9 | 9* |
| 7 | 9 | 9* |
| 8 | 9 | 9* |
| 9 | 9 | 9* |
| 10 | 9 | 9* |
| 11 | 9 | 9* |
| 12 | 9 | 9 |

I claim:
1. A method of combating rootworms of the genus Diabrotica at a locus which comprises treating the locus with an insecticidally effective amount of a composition comprising an insecticidally effective amount of a compound of the formula:

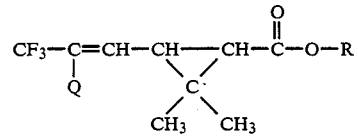

wherein Q represents fluoro or chloro and R is selected from the group consisting of 2-chloro-4-fluorobenzyl, 2-chloro-5-fluorobenzyl and 2-chloro-6-fluorobenzyl, and a carrier therefor.

2. The method of claim 1 wherein the composition consists of granules of mineral or vegetable origin coated or impregnated with an insecticidably effective amount of said compound.

3. The method of claim 2 wherein the compound is one wherein Q is chloro.

4. The method of claim 2 wherein the compound is one wherein R is 2-chloro-4-fluorobenzyl or 2-chloro-6-fluorobenzyl.

5. The method of claim 2 wherein the compound is one wherein Q is chloro and R is 2-chloro-6-fluorobenzyl.

6. The method of claim 2 wherein the compound is 2-Chloro-6-fluorobenzyl($\pm$)-cis-3-(2-chloro-3,3,3-trifluoroprop-1-en-1-yl)-2,2-dimethylcyclopropane carboxylate.

* * * * *